United States Patent [19]

Faeser

[11] Patent Number: 5,055,013
[45] Date of Patent: Oct. 8, 1991

[54] APPARATUS FOR INJECTING FLUIDS

[75] Inventor: Ulrich Faeser, Bad Homburg, Fed. Rep. of Germany

[73] Assignee: Fresenius AG, Bad Homburg, Fed. Rep. of Germany

[21] Appl. No.: 551,215

[22] Filed: Jul. 10, 1990

[30] Foreign Application Priority Data

Jul. 15, 1989 [DE] Fed. Rep. of Germany ....... 3923457

[51] Int. Cl.$^5$ .............................................. F04B 43/12
[52] U.S. Cl. .................................. 417/474; 604/153; 417/479
[58] Field of Search ............... 417/474, 475, 478, 479; 604/153; 128/DIG. 12

[56] References Cited

U.S. PATENT DOCUMENTS

| | | | |
|---|---|---|---|
| 4,236,880 | 12/1980 | Archibald | 417/479 X |
| 4,382,753 | 5/1983 | Archibald | 417/479 |
| 4,650,469 | 3/1987 | Berg et al. | 417/474 X |
| 4,657,490 | 4/1987 | Abbott | 417/479 X |
| 4,840,542 | 6/1989 | Abbott | 417/479 X |
| 4,909,710 | 3/1990 | Kaplan et al. | 417/474 X |
| 4,952,124 | 8/1990 | Ogami | 417/474 |

FOREIGN PATENT DOCUMENTS

| | | |
|---|---|---|
| 0024431 | 8/1985 | European Pat. Off. . |
| 3413437 | 4/1985 | Fed. Rep. of Germany ...... 417/474 |
| 2065789 | 7/1981 | United Kingdom . |

Primary Examiner—Leonard E. Smith
Assistant Examiner—Eugene L. Szczecina, Jr.
Attorney, Agent, or Firm—Townsend and Townsend

[57] ABSTRACT

The invention relates to an apparatus for injecting fluid in which as delivery conduit portion a simple hose segment having the same diameter throughout is used which is subjected to the action of a total of three pump rams, thereby forming delivery chambers (9-11) by compression of the hose segment, one of the pump rams (14) performing in the completely closed state the function of an outlet valve whilst having a delivery function until complete closure of the corresponding hose cross-section. As a result, in a very simple technical manner a considerable uniformization of the delivery flow is achieved.

7 Claims, 2 Drawing Sheets

APPARATUS FOR INJECTING FLUIDS

BACKGROUND OF THE INVENTION

The invention relates to an apparatus for injecting fluids.

Apparatuses for injecting fluids in the form of infusion pumps are constructed as flexible tube pumps or as pumps without tube with separate delivery chambers. In each case the continuously deliverable fluid volume is limited by the method technology. Limitation results in hose or flexible tube pumps also from the length of the delivery path and in pumps with separate delivery chamber from the volume thereof. Consequently, along with or after the delivery of the limited volume replenishment of said volume is necessary.

If a delivery of a fluid is to take place with constant flow rate a constant pressure must be maintained in the patient-side part of the transfusion apparatus.

The replenished volume is under hydrostatic pressure which is governed by the vertical level difference between fluid reservoir and delivery element. When an infusion pump is used for its intended purpose this hydrostatic pressure is always less than the fluid pressure in the delivery direction, i.e. in the patient-side part of the transfusion apparatus.

An apparatus for injecting liquids into the human body which uses a flexible conduit delivery system is known for example from EP-A-0 024 431. In this apparatus a specifically formed pump chamber is employed which is constructed as one-way pump chamber and has two so-called flexible roll diaphragm pump chambers which in the unloaded state define a predetermined volume which is reduced during the pumping operation by correspondingly formed pump rams. To achieve the desired mode of operation, such an infusion pump has two pump rams as well as an inlet valve and an outlet valve. Furthermore, a third valve piston is necessary which is not driven but moves in a pressure acquiring chamber of the pump chamber in dependence upon a fluid pressure.

If it is assumed that the delivery with constant flow rate is fulfilled via the delivery volume, finite due to the method technology, with a typical flexible delivery conduit infusion pump problems are still encountered on changing to the next delivery volume. This critical instant is reached whenever the inlet valve of a typical flexible delivery conduit infusion pump must be closed to enable the outlet valve to be opened. In a typical flexible delivery conduit infusion pump the change from one delivery phase to the next delivery phase therefore involves a temporary pressure drop in the patient-side part of the transfusion apparatus and this results in a reduction of the flow rate, i.e. a reduction of the delivery volume per unit time. This in turn reduces the accuracy of the delivery rate in particular at small values and with small measuring times of the delivery rate involves high deviations. This means in other words that small delivery rates must be maintained over a long period of time in order to achieve the desired volume delivered in unit time with an acceptable accuracy at all.

A further pump, which is identical to that of EP-A-24431, is described in GB patent 2,065,789. In this respect, similar problems arise in this case as well.

It is therefore the problem of the present invention to provide an apparatus for injecting fluids into the human body which uses a flexible conduit delivery system and which also permits an extremely uniform delivery of the medium with simultaneously small apparatus expenditure.

SUMMARY OF THE INVENTION

With the apparatus according to the invention a delivery mechanism of a peristaltic-like hose pump is provided which requires a total of only four rams which can constrict the hose against the pressure plate in cross-section until a closure of the cross-section is achieved. The hose of flexible tube returns due to the tube-inherent resetting forces to its complete cross-section when the rams move away from the pressure plate.

The particular advantages of the apparatus according to the invention include an extremely uniform delivery volume per unit time and due to the fact that the outlet valve is constructed as pump ram valve change times are eliminated. This makes the flow of the medium to be pumped uniform without having to provide a high apparatus expenditure for this purpose.

Consequently, on actuation of the delivery mechanism, three delivery chambers arise, only the inlet-side ram having valve functions.

The subsidiary claims contain advantageous further developments of the invention.

Further details, features and advantages of the invention will be apparent from the following description of an example of embodiment with the aid of the drawings.

DESCRIPTION OF SPECIFIC EMBODIMENTS

Figure 1:
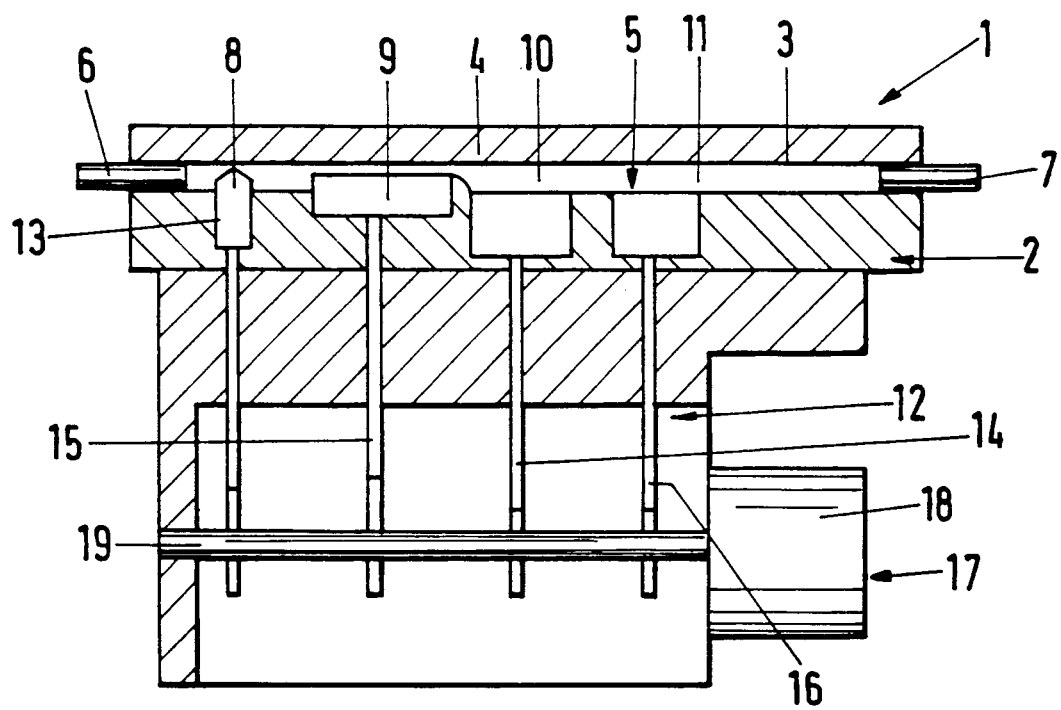
FIG. 1 is a schematic greatly simplified illustration of a possible embodiment of an apparatus according to the invention.

In FIG. 1 a greatly simplified schematic illustration of an apparatus 1 according to the invention for injecting fluid is shown, said apparatus having a housing 2 with an accommodation space 3 and a pressure plate 4. The apparatus 1 according to the invention further comprises an elastic delivery conduit portion 5 which is arranged in the accommodation space 3 and comprises an inlet 6 connectable to a feed conduit not shown in detail and an outlet 7 connectable to a discharge conduit likewise not shown in detail. In the delivery conduit portion 5 a shutoff portion 8 and delivery chambers 9 to 11 may be formed in a manner to be described in further detail.

For this purpose, the apparatus 1 according to the invention includes a delivery means 12 which has an inlet valve 13 which is arranged seen in the delivery direction downstream of the inlet 6. Furthermore, an outlet valve 14 is arranged upstream of the outlet 7. Said outlet valve 14, in contrast to hitherknown apparatuses is however constructed as pump ram so that the apparatus 1 according to the invention together with a further first and second pump ram 15 and 16 has a total of three pump rams which cyclically enlarge and diminish the delivery chambers 9 to 11, the first pump ram 15 being arranged between the inlet valve 13 and the outlet valve or pump ram 14 and the second pump ram 16 being arranged between the outlet valve or pump ram 14 and the outlet 7.

One of the particular advantages of the apparatus 1 according to the invention is that the delivery conduit portion 5 is formed as simple hose or flexible tube segment which in the state uninfluenced by the pump rams and the inlet valve has a constant diameter throughout.

The delivery chambers 9 to 11 of the apparatus according to the invention are formed by the action of the pump rams 14 to 16 which compress the hose segment 5; on retraction of the pump rams away from the pressure plate 4 the pump chambers thus formed are enlarged again up to the original cross-section of the hose segment 5 due to the inherent recovery forces of the flexible tube.

The movement of the pump rams 14 to 16 and of the inlet valve 13 is effected by a drive means 17 which in usual manner may have a motor 18 having a drive shaft 19 on which cams may be arranged which are suitably formed corresponding to the movement to be generated and time sequence of the movement of the rams.

Figure 2:
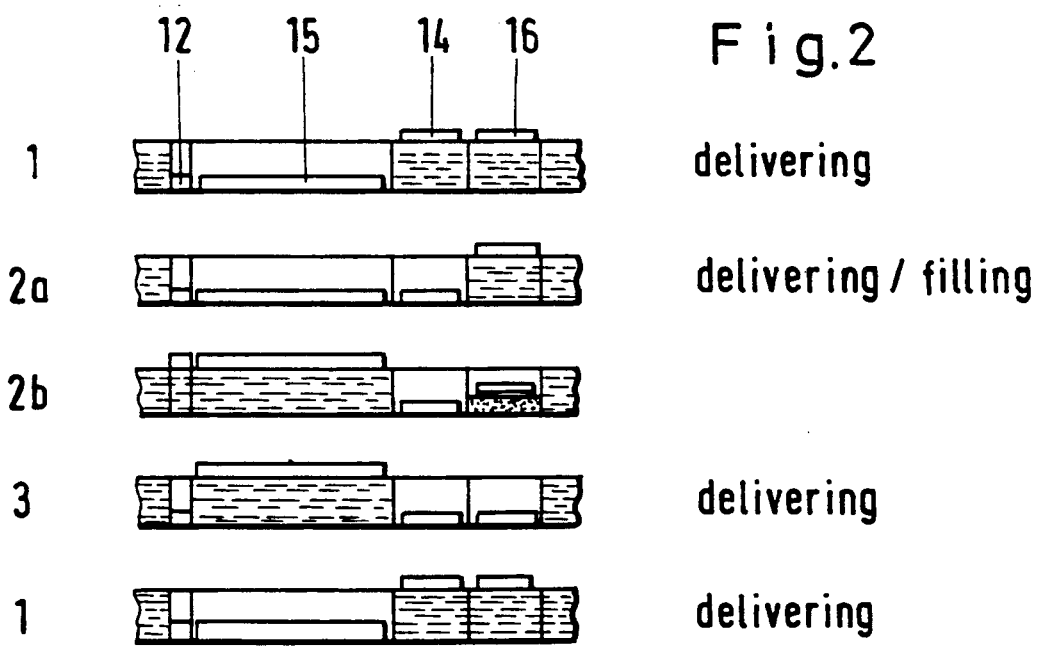
FIG. 2 is a schematic illustration of the working cycle of the apparatus according to FIG. 1.
Figure 3:
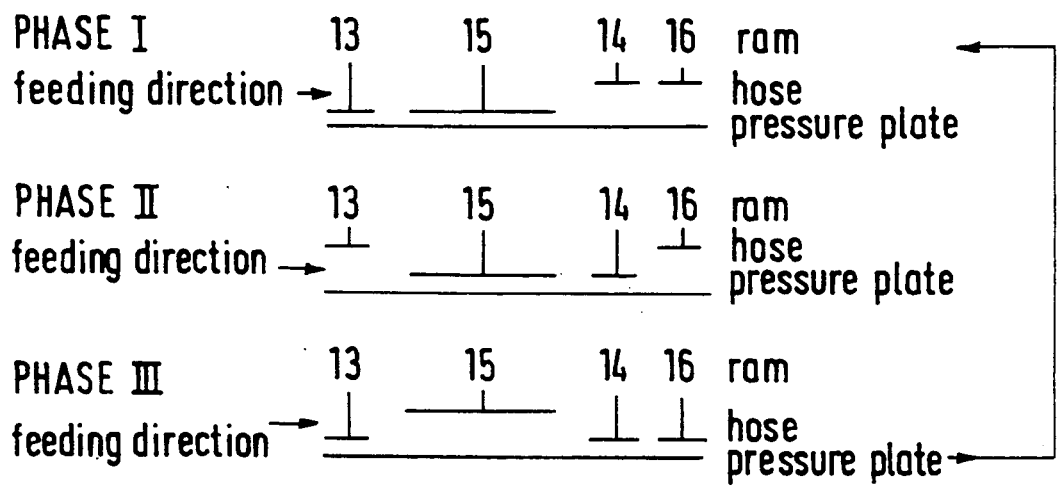
FIG. 3 is a basic sketch of the position of the rams of the apparatus according to the invention each at the start of a phase and FIG. 4 shows the phase scheme of the rams of the apparatus according to the invention associated with FIG. 3.
Figure 4:
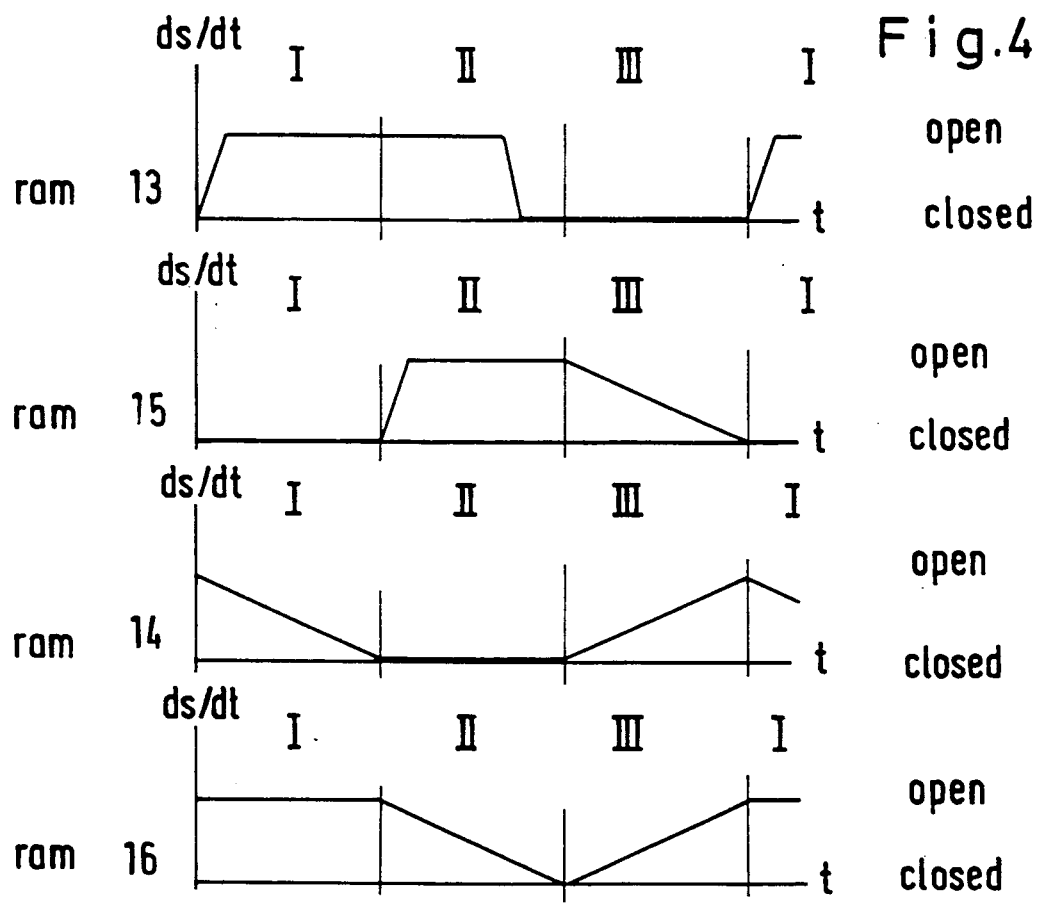

To explain the mode of operation of the apparatus according to the invention, which follows directly from consideration of FIGS. 2 to 4, the following assumptions will for example be made:

It is assumed that the possible movement velocities of the rams 13 to 16 are V1 and V2. The velocity V1 is associated with the ram or inlet valve 13 whilst the ram 15 closes with V2 and opens with V1. The rams 14 and 16 each open and close with V2, V1 being greater than V2.

Under these conditions, the phase relationships are maintained in accordance with the phase scheme illustrated in FIG. 4.

Furthermore, it is to be pointed out regarding the geometry of the rams 14 and 16 that they have a length 1 whilst the ram 15 has a length 3 1. Since the ram 13 is constructed as inlet valve its length does not fundamentally have any influence on the mode of operation.

As apparent from FIGS. 3 and 4, the ram 15 remains closed in the phase I. The ram 13 opens with V1 and the ram 14 moves with V2 until hose closure in the direction of the pressure plate 4 whilst the ram 16 remains open. The volume disposed under the ram 14 is delivered.

With phase II delivery of the volume element disposed under the ram 16 begins by closure with V2. During this phase the ram 15 is opened with V1 and the ram 13 closed with V1. This results in the filling of the tube volume disposed under the ram 15.

In phase III the rams 15, 14 and 16 move simultaneously and with the same velocity magnitudes V2. The ram 15 moves against the pressure plate 4 and the rams 14 and 16 move jointly away from the pressure plate 4. The ram 13 remains closed. As a result, due to the length ratios of the ram 15 to the ram 14 and the ram 15 to the ram 16 a volume corresponding to the lower ram 14 or lower ram 16 respectively is again delivered.

All the phases I to III are delivery phases in the patient-side part (pressure part) of the transfusion apparatus, the filling being prepared in phase I and in phase II the filling of the volumes delivered in phases I to III taking place in the pressure part with simultaneous delivery as during phases I and III. The pressure drop described with regard to a typical flexible delivery conduit infusion pump is thereby excluded, provided the conditions are maintained.

The phase sequence described above according to FIGS. 3 and 4 corresponds to the functions of the apparatus set forth in FIG. 2 in steps 1, 2a, 2b, 3 and 1.

I claim:

1. Apparatus for injecting fluid comprising:

a housing having an accommodation space and a pressure plate;

an elastic delivery conduit portion which is arranged in the accommodation space, said elastic delivery conduit portion having an inlet connectable to a feed conduit and an outlet connectable to a discharge conduit, said conduit portion having formed therein a first conveying chamber, a second conveying chamber and a third conveying chamber;

delivery means, said delivery means having an inlet valve downstream of said inlet seen in the conveying direction, an outlet valve upstream of the outlet, and at least a first pump ram and a second pump ram for cyclically enlarging and diminishing the size of the conveying chambers, the first pump ram being disposed between the inlet valve and the outlet valve and the second pump ram being disposed between the outlet valve and the outlet;

wherein said elastic delivery conduit portion is formed as hose segment which in an uninfluenced state has a substantially constant diameter throughout;

wherein the conveying chambers are formed by compression of the elastic delivery conduit portion by means of the pump rams and the outlet valve and by subsequent expansion due to the restoring forces inherent in the elastic delivery conduit portion up to the original cross-section; and wherein the outlet valve is a further pump ram which has a delivery function up to complete closure of the cross-section of the corresponding elastic delivery conduit portion wherein the pump rams have only two different allowable movement velocities V1 and V2.

2. Apparatus according to claim 1, wherein the first velocity V1 is associated with the inlet valve.

3. Apparatus according to claim 1, wherein the first pump ram is operative to close with second velocity V2 and to open with first velocity V1.

4. Apparatus according to claim 1, wherein the outlet valve and the second pump ram open and close with second velocity V2.

5. Apparatus according to claim 1, wherein first velocity V1 is associated with the inlet valve and is greater than second velocity V2.

6. Apparatus according to claim 1, wherein the second pump ram and the outlet valve are constructed as pump rams having the same length whereas the first pump ram has a length of three times the length of said second pump ram.

7. Apparatus for injecting fluid comprising:

a housing having an accommodation space and a pressure plate;

an elastic delivery conduit portion which is arranged in the accommodation space, said elastic delivery conduit portion having an inlet connectable to a feed conduit and an outlet connectable to a discharge conduit, said conduit portion having formed therein a first conveying chamber, a second conveying chamber and a third conveying chamber;

delivery means, said delivery means having an inlet valve downstream of said inlet seen in the conveying direction, an outlet valve upstream of the outlet, and at least a first pump ram and a second pump ram for cyclically enlarging and diminishing the size of the conveying chambers, the first pump ram being disposed between the inlet valve and the outlet valve and the second pump ram being disposed between the outlet valve and the outlet;

wherein said elastic delivery conduit portion is formed as hose segment which in an uninfluenced state has a substantially constant diameter throughout;

wherein the conveying chambers are formed by compression of the elastic delivery conduit portion by means of the pump rams and the outlet valve and by subsequent expansion due to the restoring forces inherent in the elastic delivery conduit portion up to the original cross-section;

wherein the outlet valve is a further pump ram which has a delivery function up to complete closure of the cross-section of the corresponding elastic delivery conduit portion; and wherein the second pump ram and the outlet valve are constructed as pump rams having the same length whereas the first pump ram has a length of three times the length of said second pump ram.

* * * * *